US012616646B2

(12) United States Patent
Belous et al.

(10) Patent No.:     US 12,616,646 B2
(45) Date of Patent:         May 5, 2026

(54) USE OF ROCHELLE SALT

(71) Applicant: SKYLAB AG, Epalinges (CH)

(72) Inventors: Elena Yur'evna Belous, Moscow (RU);
Angelina Dmitrievna Ivanova,
Moscow (RU)

(73) Assignee: SKYLAB AG, Epalinges (CH)

( * ) Notice: Subject to any disclaimer, the term of this
patent is extended or adjusted under 35
U.S.C. 154(b) by 254 days.

(21) Appl. No.: 18/699,754

(22) PCT Filed: Dec. 15, 2021

(86) PCT No.: PCT/RU2021/000571
§ 371 (c)(1),
(2) Date: Apr. 9, 2024

(87) PCT Pub. No.: WO2023/091047

PCT Pub. Date: May 25, 2023

(65) Prior Publication Data

US 2024/0398678 A1      Dec. 5, 2024

(30) Foreign Application Priority Data

Nov. 22, 2021    (RU) ........................... RU2021133982

(51) Int. Cl.
*A61K 8/365*          (2006.01)
*A61K 8/25*          (2006.01)
*A61Q 11/00*          (2006.01)

(52) U.S. Cl.
CPC ............... *A61K 8/365* (2013.01); *A61K 8/25*
(2013.01); *A61Q 11/00* (2013.01); *A61K*
*2800/28* (2013.01); *A61K 2800/522* (2013.01);
*A61K 2800/524* (2013.01)

(58) Field of Classification Search
CPC .................................. A61K 8/22; A61Q 11/00
USPC .............................................. 424/49, 53, 401
IPC ...................................................... A61Q 11/00
See application file for complete search history.

(56) References Cited

U.S. PATENT DOCUMENTS

2003/0003163 A1     1/2003  Hodosh
2006/0171907 A1*    8/2006  Scott ...................... A61Q 11/00
424/53

FOREIGN PATENT DOCUMENTS

CN       100 352 536 C     12/2007
KR       20140104530 A   *  8/2014   ............. A61K 8/365
WO       95/31175 A1     11/1995

OTHER PUBLICATIONS

Search Report in PCT/RU2021/000571 dated Jan. 27, 2023.

* cited by examiner

*Primary Examiner* — Walter E Webb
(74) *Attorney, Agent, or Firm* — Bardmesser Law Group

(57)         ABSTRACT
The present invention relates to new uses of seignette salt
and can be used in the field of dental and oral care products.

18 Claims, 2 Drawing Sheets

| Trajectory shape, range. | Insert position | Device type |
|---|---|---|
| ∞, L=25 mm | cbc (● ○ ○, ● ○ ○, ● ○ ○) | |

| Trajectory shape, range. | Insert position | Device type |
|---|---|---|
| ∞, L=25 mm | ccc (●○ ○, ●○ ○, ●○ ○) |  |

USE OF ROCHELLE SALT

FIELD OF THE INVENTION

The present invention relates to new uses of seignette salt and can be used in the field of dental care products.

PRIOR ART

The phenomenon of occurrence of electric polarization in crystals as a result of mechanical strain—or piezoelectric effect—in the recent years has become widely spread in instrumental dentistry both in dental surgical procedures and in teeth whitening [1-5]. The latter direction is based on use of ultrasound scalers [1]. Under the impact of electric current materials possessing piezoelectric properties start to deform. "Inverse piezoelectric effect" is observed. Electric pulses induce microvibrations on piezoelectric materials that can be used for oral care procedures: removal of supragingival deposits—dental tartar and plaque, subgingival deposits.

As tooth enamel whitening and tone levelling, removal of pigments from the upper dentine layer remains one of the most popular and in-demand effects of oral hygiene, and professional procedures are expensive services and take a lot of time, the authors offer a new approach to teeth cleaning and whitening as part of daily hygiene also based on piezoelectric effects.

With this aim it is offered to use substances possessing piezoelectric properties—piezoelectric materials—as components of formulations of whitening toothpastes and other oral care products [6]. The mechanism of their action during teeth brushing consists in the following. In the process of daily hygienic procedures a manual or electric toothbrush exert mechanical impact on enamel. Piezoelectric materials contained in toothpaste are ultra-sensitive to mechanical vibrations. Electric polarization takes place in such crystals in case of tension and compression in certain directions. As a result, electric charges of both signs appear on their surfaces. In some piezoelectric crystals the lattice of positive ions in the state of thermodynamic equilibrium is displaced with respect to the lattice of negative ions in such a way that the crystals are electrically polarized even in absence of an electric field. The effect of spontaneous polarization is concealed with free surface charges present in the medium. The polarization amplitude in this state will be reduced owing to negative voltage. Deformation of crystals of piezoelectric materials during teeth brushing can lead to redistribution of electric charges and release of extra-charges from the surface. As a result of getting into an aqueous medium excessive charges can lead to generation of reactive oxygen species—$\cdot OH$ and $\cdot O^{2-}$ [7]. Under maximum mechanical strain there is reduction of the number of bound (polarization) charges. Release of charges will be observed till achievement of a new equilibrium state by the piezoelectric material [8]. With reduction of the impact (change of negative voltage to positive one) polarization of the material will increase, respectively, there will be adsorption by the piezoelectric material of charge carriers isolated from the electrolyte solution. This process caused by piezoelectric properties will also lead to generation of highly active radicals $\cdot OH$ or $\cdot O^{2-}$ in the medium. Thus, the principle of whitening effect of the piezoelectric material in conditions of periodic mechanical impact in an electrolyte medium is based on formation of reactive oxygen species causing oxidative cleavage of color pigments present on enamel. The effect is similar to photocatalytic reactions activated by the radiation.

Experimental confirmation of described effects of piezoelectric materials is given in the study by Wang et al. [6]. It is shown that nanoparticles of barium titanate BaTiO3 (BTO) thanks to piezoelectric properties enable cleavage of organic colors. The results were obtained in experiments with a solution of indigo carmine used in the food industry as well as Rhodamine B under ultrasound impact imitating the teeth brushing process.

Polarized samples of BTO lead to significant enamel tone lightening in case of vibration during 3 hours, removing staining caused by black tea, blueberry juice, wine and their combinations [6]. Analysis of micromorphological characteristics of teeth revealed that piezoelectric whitening is not mechanically destructive for tooth enamel. At the same time it was shown that treatment with 3% oxygen peroxide exerts more aggressive impact on enamel. The obtained data prove that with the use of piezoelectric materials formation of highly active radicals is significantly lower than with the use of 3% hydrogen peroxide, which prevents the risk of undesirable impact on enamel during whitening by the given method.

Assessment of Vickers microhardness of tooth enamel did not reveal negative effects during treatment of teeth with piezoelectric materials.

For BTO piezoelectric material nanoparticles no cytotoxic action was revealed in experiments for smooth muscle cells of A7r5 rats [6].

In the study by Wang et al. [6] it was confirmed that whitening is basically mediated by piezoelectric effects. With the use of BTO as an active substance in non-polar and paraelectric phases when piezoelectric properties are lost the whitening effect of the substance in similar conditions was negligible [6].

Formation of reactive oxygen species is a key process of piezoelectric cleavage of compounds. Generation of radicals $\cdot OH$ or $\cdot O^{2-}$ in an aqueous medium at the example of BTO piezoelectric material was confirmed by the method of paramagnetic nuclear magnetic resonance spectroscopy. During the experiment the recorded signal was proportional to effectiveness of cleavage of organic colors.

The method of whitening offered by the authors that is based on use of piezoelectric materials enables replacing, in formulations of toothpastes, non-soluble abrasive particles with limited effectiveness and in a number of cases, specifically, in case of continuous systemic impact, can lead to appearance of scratches on enamel. Use of piezoeffects for enamel whitening, removal of pigments and deposits surpasses chemical whitening methods based on use of hydrogen peroxide in terms of safety and convenience of use. It should be noted that piezoelectric material nanoparticles demonstrate chemical, structural and electric stability, which makes it possible to introduce them in multicomponent formulations of toothpastes.

Thus, among the methods used in practice, piezoelectric whitening is the safest approach that enables delicate removal of pigments and effective enamel whitening at home.

Only ionic crystals having no symmetry center possess piezoelectric properties. The value and nature of piezoelectric effect greatly depends on the material nature as well as orientation of applied mechanical force (or electric field) in relation to its crystallographic axes[9].

All main kinds of deformations cause a change of the elementary crystal cell volume, but for most materials these changes are counterbalanced by compression [9]. Maximum deformations are characteristic for crystals of seignette salt—crystals of potassium sodium tartrate KNaC$_4$H$_4$O$_6$·4H$_2$O. Ferroelectric properties, i.e. ability of spontaneous polarization, were revealed for this substance for the first time. Similar properties are demonstrated by potassium dihydrogen phosphate (KH$_2$PO$_4$). Among crystalline compounds of interest are complex oxides described with the general chemical formula ABO$_3$ that have a structure of perovskite type (based on the name of the mineral CaTiO$_3$) [9]. The crystal of barium titanate BaTiO$_3$ was the first oxide of the perovskite family where existence of several ferroelectric phases was established [9]. Typical piezoelectric systems also include hexagonal crystals of wurtzite ZnO, 2D materials of MoS$_2$ type, the group of bismuth derivatives [10]. An example of monocrystalline weak piezoelectric material is quartz. High piezoelectric properties are characteristic for materials based on zirconate-titanates, niobates (lead, sodium-potassium) [9].

As regards development of whitening methods and formulation of toothpastes with a whitening effect one should note mentioning in literature of such piezoelectric materials as zinc oxide ZnO, strontium titanate SrTiO$_3$, barium titanate BaTiO$_3$, calcium titanate CaTiO$_3$ as well as seignette salt [6,11-17]. Zinc oxide and different titanates are offered as activated catalysts [11]. Inclusion of seignette salt in formulations is offered with different functional applications—as a compound demonstrating a synergetic effect during whitening in combination with peroxide compounds, a chelating and another auxiliary agent [12-17].

Analysis of existing whitening methods and experimental data about effectiveness of direct piezoelectric effect during removal of pigments from enamel shows that inclusion of a piezoelectric material in toothpaste formulation enables development of a safer at-home teeth whitening system. Seignette salt can be the active piezoelectric agent in toothpaste composition formulations. The substance is characterized with high piezoelectric parameters, a complex of potential treatment-and-prophylactic and antibacterial effects, has a multi-year history of use as an auxiliary component in oral care products and a favorable safety profile.

A promising direction in the field of production of toothpastes is developing formulations of complex-action oral care products, which not only clean teeth surface effectively and have prophylactic and revitalizing effects for oral cavity tissues, but also have a pleasant taste and flavoring and do not contain components that can controversially influence not only oral organs, but the human organism generally in case of permanent use, considering the probability of paste swallowing.

Seignette salt (SS) generally meets these requirements. The compound is a widely spread food additive safe for humans. In the territory of RF tartrates (potassium tartrate (E336), calcium tartrate (E354), sodium tartrate (E335), sodium-potassium tartrate (E337)) (cyclamic acid and its sodium, calcium salts) are certified as food additives and can be used in accordance with the Technical Regulations of the Customs Union TR CU 029/2012 "Safety requirements for food additives, flavoring agents and processing supplements" [18].

Seignette salt, thanks to its chemical and piezoelectric properties in toothpaste formulations, can have complex action for teeth surface and oral tissues.

Acting as a chelating agent, seignette salt is capable of binding Ca$^{2+}$ calcium ions. Ca$^{2+}$ and F$^-$ ions participate in tooth enamel mineralization and in case of a pathology increase deposition of glycoproteins on it and dental plaque formation. Dental plaque is formed by deposition of microorganisms on pellicula surface and it increases by constant overlaying of new kinds of bacteria [19]. Dental plaque calcification results in tartar formation. By chelating calcium ions SS is capable of binding oral cavity microorganisms that can form dental plaque colonies and also of inhibiting growth of calcium phosphate crystals in saliva. For an optimal cleaning effect and prevention of plaque formation the calcium ion binding constant for chelating agents in oral care products shall be about $10^1 \div 10^5$ [20].

Agents with chelating properties in multicomponent formulations that, among others, include toothpastes, also contribute to increase of stability and resistance to oxidation of the final product[20].

Particles of Seignette salt, thanks to piezoelectric properties, are capable of having a diversified mechanism of the antibacterial effect. The sterilizing effect is connected with formation of reactive oxygen species in a solution under mechanical impact on the piezoelectric material. By present, antibacterial activity has been studied for such piezoelectric materials as barium titanate, tungsten disulfide. It was revealed that effectiveness of their sterilizing action with respect to *Escherichia coli* is 99.9% with treatment duration of 20-60 minutes [10].

Under stress particles of seignette salt are capable of polarizing. In piezoelectric crystals the lattice of positive ions in the state of thermodynamic equilibrium can be displaced with respect to the lattice of negative ions in such a way that the crystals are electrically polarized even in absence of an electric field. This causes attraction of bacteria carrying the opposite surface charge to charged crystal areas [21]. Thus, it can enable removal of bacterial cells from oral cavity together with particles of seignette salt after teeth brushing process.

The state of parodontium, namely the complex of tissues surrounding the tooth: mucous membranes of gums, alveoli, dental ligamentous apparatus, greatly determines the health of teeth. At present inflammatory parodontium diseases are widely spread [22]. One of the key points of pathogenesis is such a typical pathological process as oxidative stress. It develops on condition of intensification of free radical processes, often at the background of reduced potential of the anti-oxidant system. The processes can be adjusted by use of agents of antioxidant direction [23]. One of promising methods is use of treatment and prophylactic toothpastes based on antioxidants.

Potassium-sodium tartrate—seignette salt—is known in food industry as antioxidant E337. In a comparative experiment for one of tartrates—sodium tartrate—it was established that its antioxidant activity can surpass the activity for α-tochopherol [24]. It was shown that sodium tartrate in a low concentration of 0.01% produces marked antioxidant effect on samples of different kinds of vegetable oils subjected to heating. In a parallel experiment α-tocopherol was used in the concentration of 0.1%. For α-tocopherol there are numerous experimental data proving its positive influence on the oral cavity condition thanks to antioxidant activity [25-28].

According to clinical studies data, toothpastes containing substances of antioxidant action are capable of modifying exchange of substances in the oral fluid and causing changes in metabolism of parodontium tissues [22]. Formulations with antioxidants are capable of reversing oxidative stress phenomena and can be recommended for regular use with prophylactic aims.

Thus, it is believed that the impact of seignette salt on tooth-surrounding tissues can help in elimination of metabolic disorders in the oral fluid due to antioxidant activity.

Another aspect of antioxidant activity of seignette salt can be connected with the following. A clinically important observation is reduction of adhesive properties of enamel after whitening because of hold of residual oxygen near its surface. Restoration of adhesive properties after whitening with the use of hydrogen peroxide requires minimum 2 weeks [29]. It is shown that post-treatment of the oral cavity with different antioxidants has a favorable effect on the given process [29]. It was revealed that 10% α-tocopherol is effective in at-home whitening [30]. The antioxidant in use, apart from restoration of adhesive properties of enamel after whitening, shall provide for preservation of its color stability [29]. α-tocopherol of amber color does not meet this requirement causing enamel color change. Seignette salt has no color and can effectively remove residual radicals without causing undesirable enamel tone change.

Combination of Seignette Salt and Silicon Dioxide.

Silicon dioxide is a widely spread abrasive component of toothpastes having a delicate action on tooth enamel. Particles of $SiO_2$ polish the surface, preventing dental plaque formation for a long time. Advantages of this given component are the following:

indifference to many active components;

possibility of control of abrasivity and cleaning ability within a wide range;

possibility of developing transparent toothpastes, i.e. toothpastes in which the refraction factor of the abrasive equals the refraction factor of the liquid phase in which it is suspended.

It is believed that the individual effect of each component of the combination of seignette salt and silicon dioxide will increase in case of combined use. The specified combination will prevent formation and reduce the mass of dental plaque that has already formed due to:

polishing effect of the abrasive, generation of highly active radicals and oxidation of soils as a result of piezoelectric effect, chelating properties of seignette salt enabling reduction of the concentration of excessive ions and prevention of adhesion of bacteria.

Literature provides experimental data that aerosil is capable of interacting with biologically active organic acids mechanically and chemically [31]. Potassium-sodium tartrate is a salt of polybasic tartaric acid. In case of polybasic acids molecules of absorption water of silicon dioxide serve as a link between the carrier and monomeric molecules of acids: aerosil—absorption water—polybasic acid.

Acting as a carrier, silicon dioxide can significantly modify properties of seignette salt—potentiate its antioxidant activity and increase antibacterial activity. It was shown in an experiment with different natural and synthetic antioxidants that use of mesoporous silicon dioxide, nanoparticles of silicon dioxide as a carrier leads to a synergetic effect [32]. Antimicrobial activity can be increased by numerous non-specific interactions between the bacterial cell and the surface of particles of $SiO_2$ [33].

Thus, it is believed that the combination of seignette salt and silicon dioxide, along with prevention of formation/reduction of mass of formed dental plaque and whitening, will have bactericide and deodorizing effects and will have prophylactic properties through elimination of oxidative metabolism disorders in the oral cavity. Seignette salt in the composition can act as an active component with a multiple mechanism of action resulting in positive impact on soft tissues of the oral cavity, whitening effect due to piezoelectric properties. Among piezoelectric materials, this component is most fully characterized, has proven safety and a multi-year history of use, including use in food products.

SUMMARY OF THE INVENTION

The aspects of the invention of the present application are:

Use of seignette salt in a dental and/or oral cavity care product as a whitening component. Use of seignette salt in a dental and/or oral cavity care product as a whitening component that does not cause a significant enamel surface microstructure change. Seignette salt as a whitening component does not cause a significant enamel surface microstructure change comparing to conventional peroxide systems. Use of seignette salt in a dental and/or oral cavity care product as a whitening component that does not cause a significant enamel microhardness change. Seignette salt as a whitening component does not cause a significant enamel microhardness change comparing to conventional peroxide systems. Use of any of the above mentioned aspects wherein the product is toothpaste, prophylactic toothpaste, tooth powder, a polishing teeth care product, tooth gel, chewing gum, sweet, candy, mouth rinse, whitening strip, dental floss with a coating, tooth brush with a coating, coloring gel, lacquer, syringe or dental tray containing gel or paste, whitening and/or remineralizing strips, tooth powder. Use of a combination of seignette salt and silicon dioxide in a dental and/or oral cavity care product as an abrasive. Use of a combination of seignette salt and silicon dioxide in a dental and/or oral cavity care product as a preservative. Use of seignette salt in a dental and/or oral cavity care product as an antioxidant.

Additional features and advantages of the claimed solution are described in the following disclosure and proved by the actual practice of the invention. These advantages and improvements can be achieved by intelligent agents constructed and trained following the claimed method, precisely following the disclosure, along with the accompanying claims and drawings.

BRIEF DESCRIPTION OF THE ATTACHED DRAWINGS

The accompanying drawings, which are included to provide a further understanding of the invention and are incorporated in and constitute a part of this specification, illustrate embodiments of the invention and together with the description serve to explain the principles of the invention.

DETAILED DESCRIPTION OF EMBODIMENTS OF THE INVENTION

Figure 1:
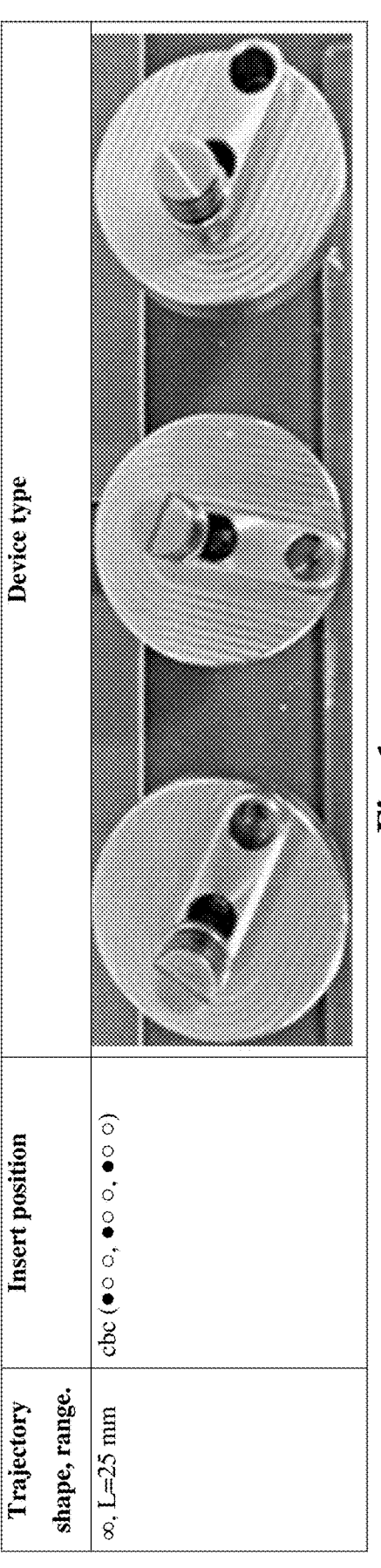
FIG. 1 illustrates working conditions of one of the experiments.

Reference will now be made in detail to the preferred embodiments of the present invention, examples of which are illustrated in the accompanying drawings.

The present invention relates to new uses of seignette salt. The aspects of the invention of the present application are the following.

Use of seignette salt in a dental and/or oral cavity care product as a whitening component.

Use of seignette salt in a dental and/or oral cavity care product as a whitening component that does not cause a significant/substantial enamel surface microstructure change. Seignette salt as a whitening component does not cause a significant/substantial enamel surface microstructure change comparing to conventional peroxide systems.

Use of seignette salt in a dental and/or oral cavity care product as a whitening component that does not cause a significant/substantial enamel microhardness change. Seignette salt as a whitening component does not cause a significant/substantial enamel microhardness change comparing to conventional peroxide systems.

Use of any of the above mentioned aspects, wherein the product is toothpaste, prophylactic toothpaste, tooth powder, a polishing teeth care product, tooth gel, chewing gum, sweet, candy, mouth rinse, whitening strip, dental floss with a coating, tooth brush with a coating, coloring gel, lacquer, syringe or dental tray containing gel or paste, whitening and/or remineralizing strips, tooth powder.

Use of a combination of seignette salt and silicon dioxide in a dental and/or oral cavity care product as an abrasive.

Use of a combination of seignette salt and silicon dioxide in a dental and/or oral cavity care product as a preservative.

Use of seignette salt in a dental and/or oral cavity care product as an antioxidant.

Embodiment of the invention can be illustrated with the following examples.

Example 1. Test of the Cleaning and Whitening Ability of FtCl (Ft Cleaning) 300

To determine resistance of dental enamel to attrition on a Martindale tester (hereinafter—Tester) the sets were analyzed—samples of solutions of piezoelectric materials and tooth brushes based on the following indicator:

FtCl (Ft Cleaning) 300, characterizes the cleaning ability of a solution (paste) by making 300 cleaning movements (mah) in a suspension of piezoelectric materials. The indicator is used as an analog of PCR (Pellicle Cleaning Ration) and it enables quantitative assessment of the cleaning and whitening action of a solution (paste) in case of a single-time cleaning.

The minimum equipment set for the tests was represented by the following instruments:

a Martindale tester (toothbrush model) produced by ATLAS;

a chroma meter KONICA MINOLTRA CR-400 or another chroma meter (spectrophotometer) with the possibility of measuring color change in Lab coordinates and with max. size of the finishing mask of =12 mm;

analytical balances with accuracy up to 0.1 mg, upper weighing limit min. 300 g;

base plates of hydroxyapatite (hereinafter—HAP base plates) based on the size of the hole in the Martindale tester brush-plate, with the whiteness value (L) 90-94;

a supersoft slate pencil KOH-I-NOOR HARDMUTH 1500 7B.

The working conditions are illustrated in FIG. 1.

Determination of FtCl300 for a solution of piezoelectric materials:

path: ∝L=25 mm,
rate 150 mah/min,
impact—300 mah,
brush load 325 g,
minimum quantity of parallel determinations—one per each paste with a test brush, a test tooth brush: tooth brush PROFESSIONAL COMPLETE of medium hardness, use one brush head for not more than 3-4 cycles, i.e. for 900-1200 mah, owing to wear out of bristles; then replace the brush head with a new one.

Test Methods.

Preparation of Base Plates of Hydroxyapatite Discs:

1) the quality of base plates is estimated—all base plates with cracks, chips, traces of any geometric deformation were excluded;

2) whiteness of the base plate surface was measured (Lin.):

3) the chromatometer was switched on and calibrated;

4) settings of the instrument measuring system were checked (this test requires Lab color coordinates);

5) a tablet was placed on the measuring table, its whiteness was measured three times;

6) sequential numbers were written on the opposite side of the tablet;

7) the base plate of hydroxyapatite discs was colored;

8) the base plate surface was carefully hatched with a supersoft slate pencil KOH-I-NOOR HARDMUTH 1500 7B in several directions;

9) the hatching was rubbed out with a thick unwaxed paper sheet and the tablet surface was polished to a shine;

10) a ready tablet has a distinctive metal shine of colored surface, the pigment has distinctive pigment adhesion to the base plate surface and does not color the expert's hands during contact and tests;

11) the whiteness of the colored base plate (Lcol) was measured.

The tester preparation for the test included the following stages:

1) individual portions of the suspension of paste in water (see the section of preparation of solutions) with the ratio of 1:2: 10 g of paste in 20 g of water were prepared for each cell;

2) the base plates were placed in holes of brush plates with their colored side up, suspensions were added. The tester was started for abrasion of base plates of colored hydroxyapatite discs.

3) the base plates were dried with filtration paper, then dried in air for 5-10 min, then—with an air blow dryer with air temperature under 40° C. during 12-15 minutes, with periodic turnovers.

FtCl300 values were calculated by the formula:

$$FtCl300=100*(Lcl-Lcol)/(Lin-Lcol)$$

Preparation of Solutions:

1. The test solution: toothpaste with seignette salt: 1 (10 ml) part of toothpaste with seignette salt—2 (20 ml) parts of distilled water;

2. Reference: toothpaste with barium titanate: 1 (10 ml) part of toothpaste with barium titanate—2 (20 ml) parts of distilled water;

3. Zinc oxide paste solution: 1 (10 ml) part of toothpaste with zinc oxide—2 (20 ml) parts of distilled water;

4. Positive control: SPLAT Special Blackwood toothpaste solution: 1 (10 ml) part of toothpaste: 2 (20 ml) parts of distilled water;

5. Negative control: 3 (30 ml) parts of water.

Formulation of test pastes (with a single concentration of different piezoelectric materials) is shown in Table 1.

TABLE 1

| Raw material, procedure | % |
|---|---|
| Purified water | 0-80 |
| Sorbitol 70% NEOSORB 70/70B | 10-30 |
| Sodium carboxylmethylcellulose Walocel CRT 2000 PA 07 | 0.5-1.5 |
| Xanthan gum Keldent | 0.1-0.5 |
| Glycerol 99.5% AAK SWEDEN AB | 1-15 |
| Potassium sodium tartrate Seignette salt/Zinc oxide/Barium titanate | 0.01-5 |
| Dry extract of Stevia PE | 0.01-1 |
| Trimethylglycine Genencare OSMS BA | 0.01-1 |
| Silicon dioxide Sorbosil TC 15 | 0.01-20 |
| Silicon dioxide Sorbosil AC 43 | 0.01-20 |
| Silicon dioxide Sorbosil AC 36 | 0.01-20 |
| Flavoring Naturally Cool Flavor 513539 T | To taste |
| Bisabolol rac | 0.01-0.5 |
| Laurylsarcosinate | 0.01-1 |

Formulation Toothpaste SPLAT® Special Blackwood®: Aqua, Hydrated Silica, Hydrogenated Starch Hydrolysate, Glycerin, Maltooligosyl Glucoside, Sodium Lauroyl Sarcosinate, Cellulose Gum, Aroma, Charcoal Powder, Capryloyl/Caproyl Methyl Glucamide, Lauroyl/Myristoyl Methyl Glucamide, Sodium Benzoate, *Stevia ebaudiana* Leaf Extract, Potassium Sorbate, Menthol, o-Cymen-5-ol, *Juniperus communis* Sprout Extract, Limonene.

Test results. The lightness level was estimated by CIE LAB scale. The Lab color model was created by the International Commission on Illumination (CIE). The color was described not in terms of elements reproduced by devices, but with the use of three components of human color vision. In this model any color is determined with lightness (L-Lightness) and two chromatic components: channel a—colors from dark green through gray to purple, channel b—colors from blue through gray to yellow. Channels a and b change from −128 to 127, while L parameter—from 0 to 100. The zero value of color components with brightness of 50 corresponds to gray color in RGB model (119,119,119). Brightness value of 100 gives white color, 0—black.

The cleaning level is assessed by FtCln300 formula, where:

Lin is the whiteness value of hydroxyapatite discs before coloring.

Lcol is the whiteness value of hydroxyapatite discs after coloring.

Lcl is the whiteness value of hydroxyapatite discs after cleaning with toothpaste solutions.

$$FtCl300 = 100*(Lcl-Lcol)/(Lin-Lcol),$$

where the main constant is L—Lightness, which with the value of 100 denotes white color, so, the higher the FtCl value is, the more effective cleaning of the surface of hydroxyapatite discs was (Table 2).

TABLE 2

| 1 cycle | | 2 cycle | |
|---|---|---|---|
| Sample No. | FtCl300 | Sample No. | FtCl300 |
| 1 (toothpaste with seignette salt) | 70.43 | 1 (toothpaste with seignette salt) | 68.78 |
| 2 (toothpaste with barium titanate) | 69.16 | 2 (toothpaste with barium titanate) | 71.34 |
| 3 (toothpaste with zinc oxide) | 56.19 | 3 (toothpaste with zinc oxide) | 54.17 |

TABLE 2-continued

| | | | |
|---|---|---|---|
| 4 (Blackwood toothpaste) | 63.85 | 4 (Blackwood toothpaste) | 67.23 |
| 5 (negative control water) | 35.70 | 5 (negative control water) | 33.45 |

| 3 cycle | | 4 cycle | |
|---|---|---|---|
| 1 (toothpaste with seignette salt) | 73.56 | 1 (toothpaste with seignette salt) | 69.98 |
| 2 (toothpaste with barium titanate) | 73.68 | 2 (toothpaste with barium titanate) | 69.3 |
| 3 (toothpaste with zinc oxide) | 58.98 | 3 (toothpaste with zinc oxide) | 56.7 |
| 4 (Blackwood toothpaste) | 64.54 | 4 (Blackwood toothpaste) | 64.26 |
| 5 (negative control water) | 30.87 | 5 (negative control water) | 34.45 |

| Δ by 4 cycles | |
|---|---|
| 1 (toothpaste with seignette salt) | 70.68 |
| 2 (toothpaste with barium titanate) | 70.87 |
| 3 (toothpaste with zinc oxide) | 56.5 |
| 4 (Blackwood toothpaste) | 64.97 |
| 5 (negative control water) | 33.61 |

Results of Experiment 1:

1) the test active ingredient was piezoelectric material seignette salt;

2) the reference toothpaste for cleaning was the high-abrasive toothpaste SPLAT Special Blackwood, which in clinical studies demonstrates the best results in whitening, equal to 2.5 tones by VITA scale;

3) the reference piezoelectric material was barium titanate, which has a typical piezoelectric tetrahedral structure and therefore is to demonstrate the best results;

4) also there was prepared toothpaste with zinc oxide, which is also a commercially available piezoelectric material.

At the end of the experiment, the best results were shown by barium titanate, which cannot be used in oral care products because of prohibition of use of barium salts in perfumery and cosmetics. With the difference of 0.19 the experiment confirmed effectiveness of seignette salt; seignette salt demonstrated better results than zinc oxide and reference toothpaste Splat Special Blackwood, which in its turn speaks of prominent cleaning abilities of the composition with seignette salt.

Example 2. Test of the Cleaning and Whitening Ability of FtCl (Ft Cleaning) 300

To determine resistance of dental enamel to attrition on a Martindale tester (hereinafter—Tester) the sets were analysed—samples of solutions of piezoelectric materials and tooth brushes based on the following indicator:

FtCl (Ft Cleaning) 300, characterizes the cleaning ability of a solution (paste) by making 300 cleaning movements (mah) in a suspension of piezoelectric materials. The indicator is used as an analog of PCR (Pellicle Cleaning Ration) and it enables quantitative assessment of the cleaning and whitening action of a solution (paste) in case of a single-time cleaning.

The minimum equipment set for the tests was represented by the following instruments:

1) a Martindale tester (toothbrush model) produced by ATLAS;

2) a chroma meter KONICA MINOLTA CR-400 or another chroma meter (spectrophotometer) with the possibility of measuring color change in Lab coordinates and with max. size of the finishing mask of =12 mm;

3) Analytical balances with accuracy up to 0.1 mg, upper weighing limit min. 300 g;

4) base plates of hydroxyapatite (hereinafter—HAP base plates) based on the size of the hole in the Martindale tester brush-plate, with the whiteness value (L) 90-94;

5) a supersoft slate pencil KOH-I-NOOR HARDMUTH 1500 7B.

Figure 2:
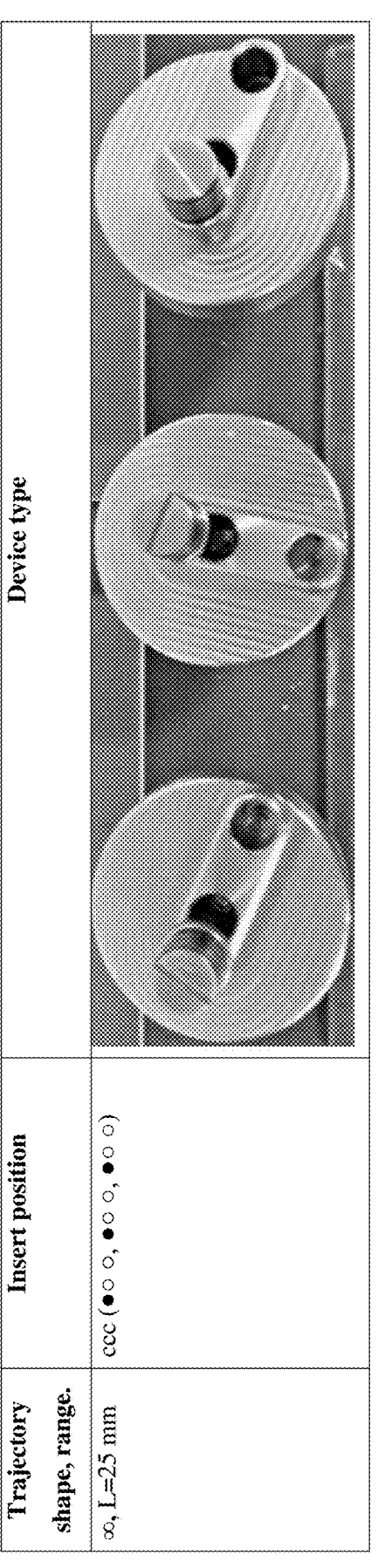
FIG. 2 illustrates working conditions of another one of the experiments.

The working conditions are illustrated in FIG. 2.

Determination of FtCl300 for a solution of piezoelectric materials:

path: ∞ L=25 mm, rate 150 mah/min, impact—300 mah, brush load 325 g, minimum quantity of parallel determinations—one per each paste with a test brush, a test tooth brush: tooth brush PROFESSIONAL COMPLETE of medium hardness use one brush head for not more than 3-4 cycles, i.e. for 900-1200 mah, owing to wear out of bristles; then replace the brush head with a new one.

Test Procedure:

Preparation of Base Plates of Hydroxyapatite Discs 1) the quality of base plates is estimated—all base plates with cracks, chips, traces of any geometric deformation were excluded.

2) whiteness of the base plate surface was measured (Lin.):

3) the chromatometer was switched on and calibrated;

4) settings of the instrument measuring system were checked (this test requires Lab color coordinates)

5) a tablet was placed on the measuring table, its whiteness was measured three times.

6) sequential numbers were written on the opposite side of the tablet.

7) the base plates of hydroxyapatite discs were colored:

8) the base plate surface was carefully hatched with a supersoft slate pencil KOH-I-NOOR HARDMUTH 1500 7B in several directions.

9) the hatching was rubbed out with a thick unwaxed paper sheet and the tablet surface was polished to a shine.

10) a ready tablet has to have a distinctive metal shine of colored surface, the pigment has to have distinctive pigment adhesion to the base plate surface and should not color the expert's hands during contact and tests.

11) the whiteness of the colored base plate (Lcol) was measured.

Tester Preparation for Tests:

1) individual portions of the suspension of paste in water (see the section of preparation of solutions) with the ratio of 1:2: 10 g of paste in 20 g of water were prepared for each cell.

2) the base plates were placed in holes of brush plates with their colored side up, suspensions were added. The tester was started for abrasion of base plates of colored hydroxyapatite discs.

3) the base plates were dried with filtration paper, then dried in air for 5-10 min, then—with an air blow dryer with air temperature under 40° C. during 12-15 minutes, with periodic turnovers.

FtCl300 values were calculated by the formula:

$$FtCl300 = 100*(Lcl-Lcol)/(Lin-Lcol)$$

Preparation of Test Solutions.

Two toothpastes with the following formulations were prepared:

1) Toothpaste free of active ingredients, with the exception of seignette salt with thickening silica—Silicon dioxide Sorbosil TC15 and abrasive silica—Silicon dioxide Sorbosil AC39, Silicon dioxide Sorbosil AC43:

Formulation: Purified water, Sorbitol, Xanthan gum, Sodium carboxymethylcellulose, Glycerol, Formulation: Seignette salt, Silicon dioxide Sorbosil TC15, Silicon dioxide Sorbosil AC39, Silicon dioxide Sorbosil AC43, Potassium sorbate+sodium benzoate, Sodium lauroylsarcosinate 2) Toothpaste free of active ingredients, with the exception of seignette salt with thickening silica—Silicon dioxide Sorbosil TC15 and without abrasive silica:

Purified water, Sorbitol, Xanthan gum, Sodium carboxymethylcellulose, Glycerol, Formulation: Seignette salt, Silicon dioxide Sorbosil TC15, Potassium sorbate+sodium benzoate, Sodium lauroylsarcosinate 3) Negative control—water (Table 3).

TABLE 3

| 1 cycle | | 2 cycle | |
|---|---|---|---|
| Sample No. | FtCl300 | Sample No. | FtCl300 |
| 1 (toothpaste with seignette salt + abrasive) | 71.80 | 1 (toothpaste with seignette salt + abrasive) | 71.42 |
| 2 (toothpaste with seignette salt w/o abrasive) | 55.68 | 2 (toothpaste with seignette salt w/o abrasive) | 54.90 |
| 3 (negative control water) | 31.29 | 3 (negative control water) | 31.45 |
| 3 cycle | | 4 cycle | |
| 1 (toothpaste with seignette salt + abrasive) | 72.3 | 1 (toothpaste with seignette salt + abrasive) | 71.44 |
| 2 (toothpaste with seignette salt w/o abrasive) | 55.9 | 2 (toothpaste with seignette salt w/o abrasive) | 55.27 |
| 3 (negative control water) | 29.16 | 3 (negative control water) | 30.6 |
| Δ by 4 cycles | | | |
| 1 (toothpaste with seignette salt + abrasive) | | | 71.74 |
| 2 (toothpaste with seignette salt w/o abrasive) | | | 55.43 |
| 3 (negative control water) | | | 30.62 |

Test results. The lightness level was estimated by CIE LAB scale.

The Lab color model was created by the International Commission on Illumination (CIE). The color was described not in terms of elements reproduced by devices, but with the use of three components of human color vision. In this model any color is determined with lightness (L-Lightness) and two chromatic components: channel a—colors from dark green through gray to purple, channel b—colors from blue through gray to yellow. Channels a and b change from −128 to 127, while L parameter—from 0 to 100. The zero value of color components with brightness of 50 corresponds to gray color in RGB model (119,119,119). Brightness value of 100 gives white color, 0—black.

The cleaning level is assessed by FtCl300 formula, where:

Lin is the whiteness value of hydroxyapatite discs before coloring.

Lcol is the whiteness value of hydroxyapatite discs after coloring.

Lcl is the whiteness value of hydroxyapatite discs after cleaning with toothpaste solutions.

FtCl300=100*(Lcl–Lcol)/(Lin–Lcol), where the main constant is L—Lightness, which with the value of 100 denotes white color, so, the higher the FtCl value is, the more effective cleaning of the surface of hydroxyapatite discs was.

As a result of the tests the toothpaste solutions demonstrated the following results (with FtCl going down):

Seignette salt+abrasive>Seignette salt w/o abrasive>negative control water.

Thus, seignette salt in combination with an abrasive system consisting of silica demonstrated the best results in cleaning the surface of hydroxyapatite discs.

Example 3. Preservation Ability Test

Two systems were tested for suppression of contamination with microorganisms by their formulations.

Two systems were seeded with the following microorganisms in specified concentrations (Tables 4 and 5).

TABLE 4

System 1: Aqueous solution with silica w/o seignette salt w/preservative - benzyl alcohol

| Kind of microorganism | Concentration of test-microorganism in contaminated sample, CFU/g Lg N/Rx Initial |
|---|---|
| *Pseudomonas aeruginosa* ATCC 9027 | $8.2 \times 10^6$ 6.9 |
| *Escherichia coli* ATCC 25922 | $7.0 \times 10^6$ 6.8 |
| *Staphylococcus aureus* ATCC 6538-P | $7.3 \times 10^6$ 6.9 |
| *Candida albicans* ATCC 10231 | $6.2 \times 10^5$ 5.8 |
| *Aspergillus brasiliensis* ATCC 16404 | $4.8 \times 10^5$ 5.7 |

TABLE 5

System 2: Aqueous solution w/silica and seignette salt w/o preservative

| Kind of microorganism | Concentration of test-microorganism in contaminated sample, CFU/g Lg N/Rx Initial |
|---|---|
| *Pseudomonas aeruginosa* ATCC 9027 | $8.0 \times 10^6$ 6.9 |
| *Escherichia coli* ATCC 25922 | $7.5 \times 10^6$ 6.9 |
| *Staphylococcus aureus* ATCC 6538-P | $7.8 \times 10^6$ 6.9 |
| *Candida albicans* ATCC 10231 | $5.6 \times 10^5$ 5.7 |
| *Aspergillus brasiliensis* ATCC 16404 | $5.3 \times 10^5$ 5.7 |

Results. After seven days the systems were analyzed for bacterial load and the following results were obtained (Tables 6 and 7):

TABLE 6

System 1: Aqueous solution w/silica w/o seignette salt w/preservative benzyl alcohol

| Kind of microorganism | Concentration of test-microorganism in contaminated sample, CFU/g Lg N/Rx | |
|---|---|---|
| | Initial | After 7 days |
| *Pseudomonas aeruginosa* ATCC 9027 | $8.2 \times 106$ 6.9 | Under 10 —/6.9 |
| *Escherichia coli* ATCC 25922 | $7.0 \times 106$ 6.8 | Under 10 —/6.8 |
| *Staphylococcus aureus* ATCC 6538-P | $7.3 \times 106$ 6.9 | Under 10 —/6.9 |
| *Candida albicans* ATCC 10231 | $6.2 \times 105$ 5.8 | Under 10 —/5.8 |
| *Aspergillus brasiliensis* ATCC 16404 | $4.8 \times 105$ 5.7 | Under 10 —/5.7 |

TABLE 7

System 2: Aqueous solution w/silica and seignette salt w/o preservative

| Kind of microorganism | Concentration of test-microorganism in contaminated sample, CFU/g Lg N/Rx | |
|---|---|---|
| | Initial | After 7 days |
| *Pseudomonas aeruginosa* ATCC 9027 | $8.0 \times 106$ 6.9 | Under 10 —/6.9 |
| *Escherichia coli* ATCC 25922 | $7.5 \times 106$ 6.9 | Under 10 —/6.9 |
| *Staphylococcus aureus* ATCC 6538-P | $7.8 \times 106$ 6.9 | Under 10 —/6.9 |
| *Candida albicans* ATCC 10231 | $5.6 \times 105$ 5.7 | Under 10 —/5.7 |
| *Aspergillus brasiliensis* ATCC 16404 | $5.3 \times 105$ 5.7 | Under 10 —/5.7 |

Conclusion: it was proven with the experiment that the preservation ability of a combination of silica and seignette salt is as effective as that of a combination of silica with benzyl alcohol preservative.

Example 4. Determination of Antioxidant Activity in Relation to Ascorbic Acid for a Liquid Sample by the Ferricyanide Spectrophotometric Method Materials and methods. The test item was 2% seignette salt solution in distilled water. The measuring was done by Ferricyanide spectrophotometric method with the use of a spectrophotometer Konika Minolta [34]

AOA—antioxidant activity $$AOA \text{ (in mol–eq/l)} = (D_0 - D_i)/1035$$

where $D_0$ is optical density of the mediator system solution in distilled water ($D_0$=1035).

$D_i$ is optical density of the mediator system solution in the test sample.

Experiment results: 2% seignette salt solution has 13.7% higher antioxidant activity comparing to vitamin C (Table 8).

<table>
<tr><td>15</td><td>16</td></tr>
</table>

TABLE 8

| | | AOA in relation to vitamin C | |
| Indicator | RD for method | mol-eq/l | % |
| --- | --- | --- | --- |
| Antioxidant activity | Ferricyanide spectrophotometric method [34] | 0.00013 | 13.7 |

It should also be appreciated that various modifications, adaptations, and alternative embodiments thereof may be made within the scope and spirit of the present invention. The invention is further defined by the following claims.

REFERENCES (ALL INCORPORATED HEREIN IN THEIR ENTIRETY)

1. Lee Y. J. et al., Development of a piezoelectric ultrasonic tooth-whitening apparatus, Trans. Electr. Electron. Mater., 2013, Vol. 14, No. 5.
2. Srinivasan S., Ganapathy D., Jain A. R., Applications of piezoelectric surgery in dentistry, Drug Invention Today, 2019, Vol. 11, No. 1.
3. Labanca M. et al., Piezoelectric surgery: Twenty years of use, Br. J. Oral Maxillofac. Surg., 2008, Vol. 46, No. 4.
4. Abella F. et al., Applications of piezoelectric surgery in endodontic surgery: A literature review, Journal of Endodontics, 2014, Vol. 40, No. 3.
5. Aly L. A. A., Piezoelectric surgery: Applications in oral & maxillofacial surgery, Futur. Dent. J., 2018, Vol. 4, No. 2.
6. Wang Y. et al. Piezo-catalysis for nondestructive tooth whitening, Nat. Commun., 2020, Vol. 11, No. 1.
7. Wu J. et al. Strong pyro-catalysis of pyroelectric BiFeO3 nanoparticles under a room-temperature cold-hot alternation, Nanoscale, 2016, Vol. 8, No. 13.
8. Zi Y. et al. Triboelectric-pyroelectric-piezoelectric hybrid cell for high-efficiency energy-harvesting and self-powered sensing, Adv. Mater., 2015, Vol. 27, No. 14.
9. Panich A. A., Marakhovsky M. A., Motin D. V., Crystalline and ceramic piezoelectric materials, Inzhenerny Vestnik Dona, 2011, Vol. 15, No. 1.
10. Tu S. et al. Piezocatalysis and Piezo-Photocatalysis: Catalysts Classification and Modification Strategy, Reaction Mechanism, and Practical Application, Advanced Functional Materials, 2020, Vol. 30, No. 48.
11. Basf Catalysts LLC, Light-activated tooth whitening composition and methods therefor, WO 2010045280.
12. Hodosh Milton, Method and composition for preventing tooth hypersensitivity when using passive bleaching agents, US 2007065376.
13. Osstemimplant co. L., Dental bleaching composition, WO 2014126351.
14. The Procter & Gamble company, Compositions and methods for improving overall tooth health and appearance, WO 2010004361.
15. Procter & Gamble, Liquid tooth-paste compositions, WO 2004032889.
16. Procter & Gamble, Oral compositions, WO 9531174.
17. Procter & Gamble, Compositions for personal hygiene, ensuring increased sensation of cold, WO2010059289.
18. Technical Regulations of the Customs Union TR CU 029/2012., Safety requirements of food additives, flavouring agents and processing supplements, 2012.
19. Scheie A. A. Mechanisms of dental plaque formation, Advances in dental research, 1994, Vol. 8, No. 2.
20. Ramji N et al., Whole mouth malodor control by a combination of antibacterial and deodorizing agents, WO 2011123601 A2.
21. Yamamoto M., Composition for oral care, JP 2013023446 A.
22. Faroponova E. A., Possibilities of elimination of metabolic disorders in the oral fluid using hygienic products with antioxidant activity, Modern problems of science and education, 2016, No. 4, P. 49.
23. Nikolaev I. V. et al., Antioxidant and peroxidase activity of saliva in inflammatory periodontal diseases and possibility of their treatment, Biomeditsinskaya Khimiya (Biomedical Chemistry), 2008, Vol. 54, No. 4, pp. 454-462.
24. Endo Y., Yamadera Y., Tsukui T., Antioxidant effects of pH-regulating agents on the thermal deterioration of vegetable oils, J. Oleo Sci, 2014, Vol. 63, No. 8.
25. Asad Iqubal M. D. et al., Role of vitamin E in prevention of oral cancer:—A review, Journal of Clinical and Diagnostic Research, 2014, Vol. 8, No. 10.
26. Shetti A., Keluskar V., Aggarwal A., Antioxidants: Enhancing oral and general health, J. Indian Acad. Oral Med. Radiol., 2009, Vol. 21, No. 1.
27. San Miguel S. M. et al., Use of antioxidants in oral healthcare, Compendium of continuing education in dentistry (Jamesburg, N. J.: 1995), 2011, Vol. 32, No. 2.
28. Vargas F. D. S. et al., Protective effect of alpha-tocopherol isomer from vitamin e against the H2O2 induced toxicity on dental pulp cells, Biomed Res. Int., 2014, Vol. 2014.
29. Degirmenci A. et al., Evaluation the effect of different antioxidants applied after bleaching on teeth color stability, Brazilian Dent. Sci., 2020, Vol. 23, No. 4.
30. Kavitha M. et al., Comparative evaluation of superoxide dismutase, alpha-tocopherol, and 10% sodium ascorbate on reversal of shear bond strength of bleached enamel: An in vitro study, Eur. J. Dent., 2016, Vol. 10, No. 1.
31. Vorsina I. A. et al., Mechano-chemical interaction of silicon dioxide with organic acids, Chemistry in interests of sustainable development, 2011, Vol. 19. pp. 485-494.
32. Khalil I. et al., Nanoantioxidants: Recent trends in antioxidant delivery applications, Antioxidants, 2020, Vol. 9, No. 1.
33. Tomina V. V. et al., Diverse Pathway to Obtain Antibacterial and Antifungal Agents Based on Silica Particles Functionalized by Amino and Phenyl Groups with Cu(II) Ion Complexes, ACS Omega, 2020, Vol. 5, No. 25.
34. Determination of antioxidant activity of electrochemically activated water by potentiometric and spectrophotometric methods. Nekrasova L. P., Mikhailova R. N., Ryzhova I. N., International Journal of Applied and Fundamental Studies, No. 5, 2016, pp. 559-563.

What is claimed is:

1. A toothpaste, comprising:
purified water 20-80 wt %;
thickener 0.5-1.5 wt %;
potassium sodium tartrate (seignette salt) 0.01-5 wt %;
abrasive 0.01-20%;
preservative 0.01-0.5 wt %; and
surfactant 0.01-1 wt %.

2. The toothpaste of claim 1, further comprising glycerol 1-15 wt %.

3. The toothpaste of claim 1, further comprising moisturizer 10-30 wt %.

4. The toothpaste of claim 3, wherein the moisturizer is sorbitol.

5. The toothpaste of claim 1, wherein the thickener is sodium carboxylmethylcellulose.

6. The toothpaste of claim 5, further comprising a second thickener of xanthan gum 0.1-0.5 wt %.

7. The toothpaste of claim 1, further comprising a dry extract of *Stevia* 0.01-1 wt %.

8. The toothpaste of claim 1, further comprising a sweetener 0.01-1 wt %.

9. The toothpaste of claim 1, further comprising trimethylglycine 0.01-1 wt %.

10. The toothpaste of claim 1, wherein the abrasive is silicon dioxide.

11. The toothpaste of claim 1, wherein the surfactant is lauroylsarcosinate.

12. The toothpaste of claim 1, wherein the preservative is bisabolol.

13. The toothpaste of claim 1, wherein the seignette salt is 0.1-2.5 wt %.

14. The toothpaste of claim 1, wherein the seignette salt is 0.5-1.5 wt %.

15. A toothpaste, comprising:

water 20-80 wt %;

potassium sodium tartrate (seignette salt) 0.01-5 wt %;

abrasive 0.01-30 wt %; and surfactant 0.01-1 wt %.

16. The toothpaste of claim 15, further comprising a thickener 0.5-1.5 wt %.

17. The toothpaste of claim 15, further comprising a preservative 0.01-0.5 wt %.

18. The toothpaste of claim 15, wherein the abrasive is 0.01-20 wt %.

\* \* \* \* \*